(12) United States Patent
Zhou

(10) Patent No.: US 8,951,988 B2
(45) Date of Patent: Feb. 10, 2015

(54) AZIDOTHYMIDINE QUINOLINE CONJUGATED COMPOUND, PREPARATION METHOD THEREFOR AND APPLICATION THEREOF IN ANTI-HEPATOMA THERAPY

(75) Inventor: Qibing Zhou, Wuhan (CN)

(73) Assignee: Huazhong University of Science and Technology, Wuhan (CN)

( * ) Notice: Subject to any disclaimer, the term of this patent is extended or adjusted under 35 U.S.C. 154(b) by 0 days.

(21) Appl. No.: 14/346,496

(22) PCT Filed: Jun. 15, 2012

(86) PCT No.: PCT/CN2012/077030
§ 371 (c)(1),
(2), (4) Date: May 22, 2014

(87) PCT Pub. No.: WO2013/123745
PCT Pub. Date: Aug. 29, 2013

(65) Prior Publication Data
US 2014/0256670 A1    Sep. 11, 2014

(30) Foreign Application Priority Data

Feb. 24, 2012  (CN) .......................... 2012 1 0043990

(51) Int. Cl.
*C07H 19/06* (2006.01)
*C07H 19/073* (2006.01)
*C07H 1/00* (2006.01)

(52) U.S. Cl.
CPC *C07H 19/06* (2013.01); *C07H 1/00* (2013.01); *C07H 19/073* (2013.01)
USPC .......................................... 514/50; 536/28.53

(58) Field of Classification Search
CPC .................................. C07H 19/06; C07H 1/00
See application file for complete search history.

(56) References Cited

U.S. PATENT DOCUMENTS

2009/0149551 A1*  6/2009  Zhou et al. ................... 514/680

FOREIGN PATENT DOCUMENTS

CN           1343673 A       4/2012

OTHER PUBLICATIONS

PCT International Search Report in International application No. PCT/CN2012/077030, published Nov. 29, 2012.

* cited by examiner

*Primary Examiner* — Scarlett Goon
*Assistant Examiner* — Bahar Craigo
(74) *Attorney, Agent, or Firm* — Davis Wright Tremaine, LLP

(57) ABSTRACT

The invention provides the Zidovudine-conjugated quinoline compound N-((1-(2-(hydroxy-methyl)-5-(5-methyl-2,4-dioxo-3,4-dihydropyrimidin-1(2H)-yl)-tetrahydrofuran-3-yl)-1H-1,2,3-triazol-4-yl)methyl)-6-(4b,8,8-trimethyl-4b,5,6,7,8,8a-hexahydrodibenzo[a,c]phenazin-2-yloxy)hexanamide. The compound can selectively kill hepatoma cells, especially hepatoma cells with hepatitis B, and inhibit the growth of subcutaneous tumors in mice, but has no significant toxicity to normal liver cells. Experiments confirm that the compound has an anti-hepatoma effect and can be used in preparation of anti-hepatoma drugs.

9 Claims, 9 Drawing Sheets

(a)

(b)

AZIDOTHYMIDINE QUINOLINE CONJUGATED COMPOUND, PREPARATION METHOD THEREFOR AND APPLICATION THEREOF IN ANTI-HEPATOMA THERAPY

CROSS-REFERENCE TO RELATED APPLICATIONS

The present application is a U.S. National Stage entry under 35 U.S.C. §371 of International Application No. PCT/CN2012/077030, filed on Jun. 15, 2012, designating the United States of America and published in Chinese on Aug. 29, 2013, which in turn claims priority to Chinese Application No. 201210043990.8, filed on Feb. 24, 2012, each of which is hereby incorporated by reference in its entirety.

TECHNICAL FIELD

The invention relates to the chemical and medical fields, and more particularly to a quinoline Zidovudine-conjugated compound, a method for preparing the same, and application thereof in anti-hepatoma therapy.

BACKGROUND OF THE INVENTION

China is a country with high incidences of hepatoma. There are approximately 350,000 cases of newly discovered hepatoma each year, accounting for about 50% of the world's new hepatoma cases. There are 300,000 cases of death caused by hepatoma each year, and the mortality rate thereof is the second highest in cancer patients in China. A main reason for this high mortality is that most patients with hepatoma are already in advanced stage of disease upon diagnosis. The existing treatment methods, include surgery, intervention and radiation therapies, are unable to effectively improve the survival rate of patients with advanced hepatoma (the 5-year survival rate is approximately 20%). Current chemotherapy drugs for cancer such as fluorouracil, doxorubicin and cisplatin are not effective in hepatoma treatment and have toxic side effects. Nexavar (sorafenib), developed and produced by the German company Bayer in 2008, is the only approved drug for advanced hepatoma so far. However, it only temporarily delays the progression of hepatoma.

Clinically, more than 70% of the patients in China with advanced hepatoma are HBV (hepatitis B virus) positive. In recent years, studies have shown that HBV gene fragments integrate into the genome of hepatoma patients at different sites with different levels, resulting in changes in the regulation of multiple molecular pathways in cells, as the carcinogenesis process. Based on these findings, targeting abnormal molecular pathways in HBV integrated hepatoma cells is a new direction of chemotherapy drugs to selectively kill hepatoma cells for hepatoma. For example, the level of cytosolic thymidine kinase (TK1) is closely related to the expression of cell division cycle. In normal cells, it is expressed only in the S phase and rapidly degraded upon entering the G2 phase. Thus, the expression level of thymidine kinase in normal liver cells is too low to detect. However, it has been found persistently in cancer patients that thymidine kinase is highly expressed, which is consistent with the rapid growth of cancer cells. Therefore, thymidine kinase is considered to be one of the important targets for cancer treatment in recent years. Agents such as Zidovudine (AZT) and Acyclovir can be converted into the corresponding 5'-phosphate by the high expression of thymidine kinase, resulting in the inhibition of viral polymerase to prevent viral nucleic acid synthesis. However, acyclovir and zidovudine are not effective in cancer treatment, mainly because they only selectively inhibit the viral polymerase. Currently, Zidovudine derivatives have been reported as potent inhibitors of thymidine kinase, yet no significant biological effect thereof is found in cancer cells. Therefore, it is critical to design novel chemical molecules for selectively killing HBV-integrated cancer cells with high expression of thymidine kinase.

SUMMARY OF THE INVENTION

The objective of the invention is to provide a novel compound with an anti-hepatoma function, and a method for preparing the same.

The invention is implemented as follows:

The invention provides a compound represented by formula (I):

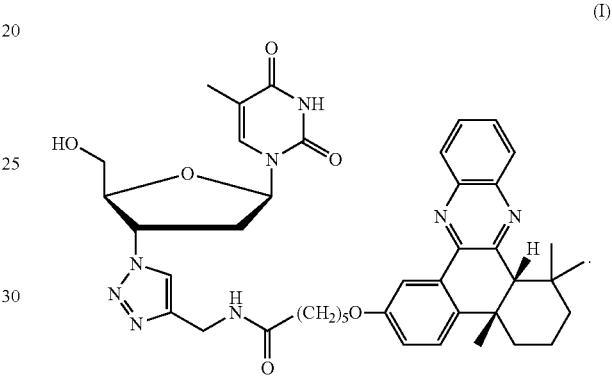

The name of the compound is (N-((1-(2-(hydroxymethyl)-5-(5-methyl-2,4-dioxo-3,4-dihydro-pyrimidin-1(2H)-yl)-tetrahydrofuran-3-yl)-1H-1,2,3-triazol-4-yl)methyl)-6-(4b,8,8-trimethyl-4-b,5,6,7,8,8a-hexahydrodibenzo[a,c]phenazin-2-yloxy)hexanamide). In the present invention, the abbreviation of the compound is AZT-QX, or a compound represented by the formula (I).

Synthesis of AZT-QX is accomplished via a click reaction. The synthetic route is shown in the following scheme:

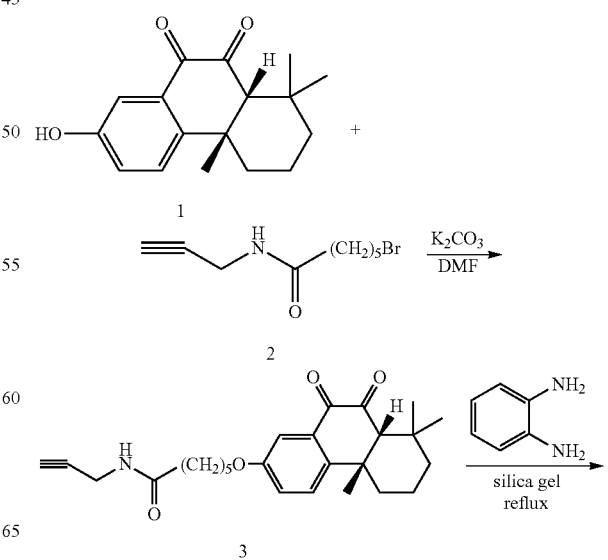

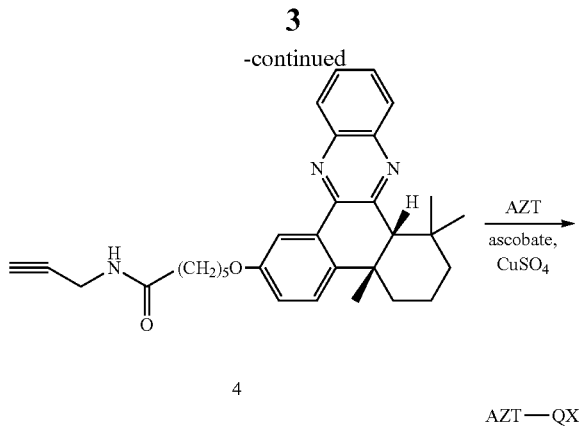

4

In the synthetic scheme above, compound 1 is 4b,5,6,7,8,8a-cis-hexahydro-2-hydroxy-4-b,8,8a-trimethyl-phenanthrene-9,10-dione; compound is bromoalkyne compound 6-bromo-N-(prop-2-ynyl)hexanamide; compound 3 is N-(prop-2-ynyl)-6-(4b, 8,8-trimethyl-9,10-dioxo-4-b,5,6,7,8,8a,9,10-octahydrophenanthren-2-yl oxy)hexanamide; compound 4 is N-(prop-2-ynyl)-6-(4b,8,8-trimethyl-4-b,5,6,7,8,8a-hexahydrodibenzo[a,c]phenazin-2-yloxy)-hexanamide; the product AZT-QX is (N-((1-(2-(hydroxymethyl)-5-(5-methyl-2,4-dioxo-3,4-dihydro-pyrimidin-1(2H)-yl)-tetrahydrofuran-3-yl)-1H-1,2,3-triazol-4-yl)methyl)-6-(4b,8,8-trimethyl-4-b,5,6,7,8,8a-hexahydrodibenzo[a,c]phenazin-2-yloxy)hexanamide).

Firstly, 4b,5,6,7,8,8a-cis-hexahydro-2-hydroxy-4-b,8,8a-trimethyl-phenanthrene-9,10-dione and bromoalkyne compound 6-bromo-N-(prop-2-ynyl)hexanamide produce compound 3 through a substitution reaction in a DMF solution under alkaline conditions (compound 3 as shown in scheme above); compound 3 is then condensed with o-phenylenediamine under reflux conditions to compound 4 (compound 4 as shown in scheme above); the resulting compound 4 is coupled with Zidovudine in organic solvent to obtain product AZT-QX through a click reaction catalyzed by monovalent copper ions (as shown in the scheme above).

A method for preparing the compound AZT-QX represented by the formula (I) comprises the following steps:

Step 1: adding 4b,5,6,7,8,8a-cis-hexahydro-2-hydroxy-4-b,8,8a-trimethyl-phenanthrene-9,10-dione and bromo alkyne into DMF solution under alkaline conditions, thereby obtaining compound N-(prop-2-ynyl)-6-(4b,8,8-trimethyl-9,10-dioxo-4-b,5,6,7,8,8a,9,10-octahydrophenanthren-2-yl oxy) hexanamide through a substitution reaction;

Step 2: condensing the mixture of compound N-(Prop-2-ynyl)-6-(4b,8,8-trimethyl-9,10-dioxo-4-b,5,6,7,8,8a,9,10-octahydrophenanthren-2-yl oxy)hexanamide and o-phenylenediamine under reflux conditions, performing dehydration to obtain compound N-(prop-2-ynyl)-6-(4b,8,8-trimethyl-4-b,5,6,7,8,8a-hexahydrodibenzo[a,c]phenazin-2-yloxy)-hexanamide;

Step 3: adding N-(prop-2-ynyl)-6-(4b,8,8-trimethyl-4-b,5,6,7,8,8a-hexahydrodibenzo[a,c]phenazin-2-yloxy)-hexanamide and Zidovudine in organic solvent, and performing a click reaction to obtain the compound AZT-QX.

In the preparation method above: the process of adding 4b,5,6,7,8,8a-cis-hexahydro-2-hydroxy-4-b,8,8a-trimethyl-phenanthrene-9,10-dione and bromoalkyne into DMF solution under alkaline conditions, thereby obtaining N-(prop-2-ynyl)-6-(4b, 8,8-trimethyl-9,10-dioxo-4-b,5,6,7,8,8a,9,10-octahydrophenanthren-2-yloxy) hexanamide through a substitution reaction in step 1 comprises adding propargylamine hydrochloride, triethylamine and 1-(3-dimethylaminopropyl)-3-ethylcarbodiimide into the solution of 6-bromohexanoic acid and dichloromethane, performing an amidation reaction at room temperature and under $N_2$ for 16 hours, then extracting the resulting solution with dichloromethane; the resulting solution is concentrated and purified by $SiO_2$ gel, producing bromoalkyne compound 6-bromo-N-(prop-2-ynyl)hexanamide; then dissolving the obtained 6-bromo-N-(prop-2-ynyl)hexanamide in DMF, and adding to the resulting solution 4b,5,6,7,8,8a-cis-hexahydro-2-hydroxy-4-b,8,8a-trimethyl-phenanthrene-9,10-dione 355 mg [See specific synthesis method: Zhou, et al. Chem. Res. Toxicol. 2008,21,732-738] and potassium carbonate to perform a substitution reaction under $N_2$ for 16 hours at room temperature. The resulting solution is extracted with dichloromethane and concentrated and purified by $SiO_2$ gel, thereby obtaining N-(prop-2-ynyl)-6-(4b,8,8-trimethyl-9,10-dioxo-4-b,5,6,7,8,8a,9,10-octahydrophenanthren-2-yl oxy)hexanamide.

The process of adding compound N-(prop-2-ynyl)-6-(4b,8,8-trimethyl-9,10-dioxo-4-b,5,6,7,8,8a,9,10-octahydrophenanthren-2-yl oxy)hexanamide and o-phenylenediamine condensed under reflux condition, and performing condensation to obtain compound N-(prop-2-ynyl)-6-(4b,8,8-trimethyl-4-b,5,6,7,8,8a-hexahydrodibenzo[a,c]phenazin-2-yloxy)-hexanamide in step 2 comprises dissolving the obtained compound in Step 1 N-(prop-2-ynyl)-6-(4b,8,8-trimethyl-9,10-dioxo-4-b,5,6,7,8,8a,9,10-octahydrophenanthren-2-yl oxy)hexanamide in toluene, to the resulting solution, adding o-phenylenediamine and $SiO_2$, performing a reaction under $N_2$ refluxing for 18 hours, then concentrating and purifying the resulting solution by $SiO_2$ gel, thereby obtaining the compound N-(prop-2-ynyl)-6-(4b,8,8-trimethyl-4-b,5,6,7,8,8a-hexahydrodibenzo[a,c]phenazin-2-yloxy)-hexanamide.

The process of adding N-(prop-2-ynyl)-6-(4b,8,8-trimethyl-4-b,5,6,7,8,8a-hexahydrodibenzo[a,c]phenazin-2-yloxy)-hexanamide and Zidovudine in organic solvent, and performing a click reaction to obtain compound AZT-QX catalyzed by monovalent copper ions in step 3 comprises dissolving the compound obtained in Step 2 N-(prop-2-ynyl)-6-(4b,8,8-trimethyl-4-b,5,6,7,8,8a-hexahydrodibenzo[a,c]phenazin-2-yloxy)-hexanamide in 5 ml DMF solution and dichloromethane, to the resulting solution adding Zidovudine and an aqueous solution of sodium ascorbate, the reaction mixture being purged with $N_2$ for 5 min to remove oxygen, and then adding $CuSO_4$ to perform a click reaction at room temperature under $N_2$ for 16 hours, then extracting the reaction mixture with dichloromethane, and concentrating and purifying by $SiO_2$ gel, thereby obtaining the compound AZT-QX.

Structural characterization of the compound AZT-QX provided by the invention: $^1H$ NMR (DMSO-$d_6$, 400 MHz): δ=11.35 (s, 1H; OH), 8.34 (t, $^3J(H, H)$=5.5 Hz, 1H; CH), 8.14-8.11 (m, 2H; 2CH), 8.06-8.04 (m, 1H; CH), 7.96 (d, $^4J(H, H)$=2.8 Hz, 1H; CH), 7.79 (m, 3H; 2CH, NH), 7.39 (d, $^3J(H, H)$=8.7 Hz, 1H; CH), 7.11 (dd, $^3J(H, H)$=8.5 Hz, $^4J(H, H)$=2.8 Hz, 1H; CH), 6.40 (t, $^3J(H, H)$=6.6 Hz, 1H; CH), 5.36-5.33 (m, 1H; CH), 5.28 (t, $^3J(H, H)$=5.2 Hz, 1H; NH), 4.31 (d, $^3J(H, H)$=5.5 Hz, 2H; $CH_2$), 4.18 (m, 1H; CH), 4.06 (t, $^3J(H, H)$=6.4 Hz, 2H; $CH_2$), 3.67-3.60 (m, 2H; $CH_2$), 2.85 (s, 1H; CH), 2.67-2.57 (m, 2H; $CH_2$), 2.16 (t, $^3J(H, H)$=7.4 Hz, 2H; $CH_2$), 1.79-1.62 (m, 5H; $CH_3$, $CH_2$), 1.56-1.43 (m, 10H; $5CH_2$), 0.93 (s, 3H; $CH_3$), 0.91 (s, 3H; $CH_3$), 0.07 ppm (s, 3H; $CH_3$); $^{13}C$ NMR (DMSO-$d_6$, 100.6 MHz): δ=172.0, 163.6, 157.4, 154.2, 150.4, 147.5, 145.2, 141.1, 140.9, 137.1, 136.1, 134.1, 129.5, 129.4, 128.9, 128.4, 125.3, 122.4, 117.7, 110.8, 109.5, 84.4, 83.8, 67.4, 60.6, 59.0, 58.5, 41.2, 37.0, 36.8, 35.5, 35.1, 34.9, 34.4, 34.0, 31.3, 28.5, 25.2, 24.9, 21.6, 18.5, 12.2 ppm; HRMS calcd for $C_{42}H_{51}N_8O_6$ $[M+H]^+$ 763.3932. found 763.3959.

The AZT-QX provided by the invention can selectively kill hepatoma cells, especially hepatoma cells with hepatitis B; the mechanism thereof is relevant to the high expression of thymidine kinase and the suppression of DNA synthesis. The selectivity of AZT-QX for hepatoma cells is achieved by part of the Zidovudine molecular structure, while the quinoline part of the structure is the functional group killing the hepatoma cells. Meanwhile, the invention illustrates that AZT-QX can inhibit the growth of subcutaneous tumors in mice and has no significant toxicity to normal liver cells, proving the compound has anti-hepatoma effect, which can be used in the preparation of anti-hepatoma drugs. The AZT-QX compound provided by the invention can be used as an active ingredient, and pharmaceutically acceptable carriers, excipients and/or additives can produce drug formulations for hepatoma treatment.

Experimental Data

Major chemicals and reagents: Sigma-Aldrich (WI, USA), J&K Scientific Ltd., Aladdin Reagent Co., Ltd, Sinopharm Chemical Reagent Co., Ltd, etc. The main equipment: Bruker Avance-400 NMR spectrometer and Thermo Fisher TSQ Quantum Max Triple Stage Quadrupole mass Spectrometer, etc.

Viability Study of Cells:

Cell culture: cancer cell lines HepG2 and Hep3B are obtained from ATCC (VA, USA), Human liver cells HL-7702 and murine liver cancer cells H22 are obtained from Shanghai Institute of Life Science Cell Culture Center (Shanghai, China). All the cells are maintained in high glucose DMEM or RPMI-1640 medium (Invitrogen, GA, USA) supplemented with 10% heat-inactivated fetal bovine serum (FBS), 25 mM HEPES, 2 mM L-glutamine, 0.1 mM nonessential amino acids, 1.0 mM sodium pyruvate, 50 U/mL penicillin, and 50 ug/ml streptomycin at 37° C. and 5% $CO_2$.

Methods of cell viability assay: liver cells are seeded on 96-well plates, AZT-QX, Zidovudine, quinoline piperazine derivatives and doxorubicin are added in respectively, the concentration thereof are from 1 nM to 200 mM. After 72 hours, an MTT assay is carried out to determine the cell viability [See method in: Zhou, et al. Chem. Res. Toxicol. 2008, 21, 732-738.].

Synthesis of AZT-QX is achieved via a click reaction (See synthetic scheme above). The comparison compound quinoline piperazine derivative (See structure in FIG. 2) (hereinafter referred to as pip-QX) synthesis is achieved according to the following synthetic route:

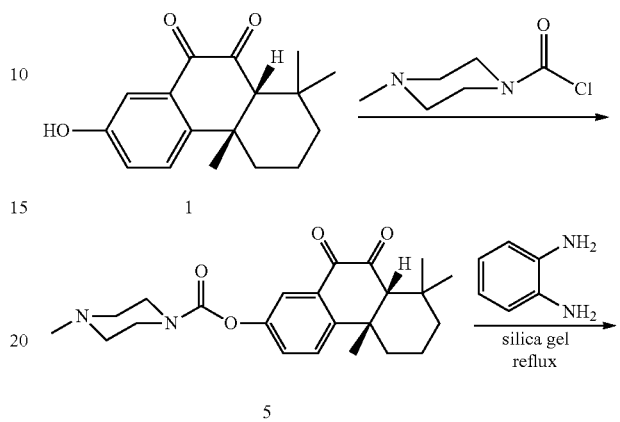

The results of the cell viability experiment are shown in FIG. 3.

Liver Tumor Model Experiment on Mice:

Liver tumor model: established by subcutaneously injecting mice H22 liver cancer cells to 9 BALB/c mice [see specific method: Li, et al. Cancer Research 2011, 301,212-220].

Animal groups and drug administration: mice are divided into 3 groups once tumors reach an average size of 8.8×8.8 mm. Group A are blank; Group B are administered AZT-QX; Group C are administered Zidovudine. On day 1 and day 7, 3 groups are injected with saline 100 μl, 50 uM Zidovudine 100 μl and 50 μM AZT-QX 100 μl (AZT-QX is prepared as the Example 2), respectively.

Animal experimental data are illustrated in the following Table 1, in which:

Group A is a blank control; Group B is compound AZT-QX; Group C is Zidovudine.

TABLE 1

| | | Group A | | | Group B | | | group C | | |
|---|---|---|---|---|---|---|---|---|---|---|
| | | L-00-R-0 | R-00 | — | L-0 | R-000 | L0-R-00 | L-00 | 1-00' | 10-R-00 |
| Day 1 | BW | 28.1 | 28.2 | 32 | 30.7 | 35.4 | 26.9 | 29.9 | 31.9 | 26.9 |
| | size | 9×9 | 8×8 | 9×10 | 8×8 | 9×8 | 10×10 | 9×9 | 9×10 | 7×9 |
| | volume | 364.5 | 256 | 405 | 256 | 288 | 500 | 364.5 | 405 | 220.5 |
| Day 2 | BW | 28.3 | 30.6 | 33.6 | 31.7 | 36.3 | 27.7 | 31.5 | 32 | 26.8 |
| | size | 8×10 | 8×9 | 9×10 | 9×9 | 9×8 | 8×9 | 10×11 | 9×10 | 7×10 |
| | volume | 320 | 288 | 405 | 364.5 | 288 | 288 | 550 | 405 | 245 |
| Day 3 | BW | 28.7 | 31.7 | 33.4 | 32 | 36 | 27.6 | 31.5 | 31.8 | 26.8 |
| | size | 13×12 | 9×9 | 10×12 | 10×10 | 9×10 | 8×9 | 11×11 | 10×12 | 8×10 |
| | volume | 936 | 364.5 | 600 | 500 | 405 | 288 | 665.5 | 600 | 320 |
| Day 4 | BW | 29 | 32.2 | 33.7 | 32.5 | 37.1 | 28 | 31.4 | 33 | 27.2 |
| | size | 12×12 | 9×11 | 11×16 | 10×10 | 9×9 | 9×10 | 11×12 | 11×13 | 10×13 |
| | volume | 864 | 445.5 | 968 | 500 | 364.5 | 405 | 726 | 786.5 | 650 |
| Day 5 | BW | 29.4 | 31.6 | 34.2 | 32.4 | 32.9 | 28.2 | 31.3 | 32.7 | 27 |
| | size | 13×12 | 7×13 | 11×16 | 11×11 | 9×9 | 9×11 | 12×13 | 11×13 | 9×12 |
| | volume | 936 | 318.5 | 968 | 665.5 | 364.5 | 445.5 | 936 | 786.5 | 486 |
| Day 6 | BW | 29.3 | 30.8 | 34.1 | 32.2 | 37 | 28.1 | 31.3 | 33.8 | 27.4 |
| | size | 12×13 | 8×13 | 12×19 | 12×13 | 9×10 | 10×11 | 13×14 | 14×15 | 11×17 |
| | volume | 936 | 416 | 1368 | 936 | 405 | 550 | 1183 | 1470 | 1028.5 |
| Day 7 | BW | 29.5 | 31.3 | 33.4 | 32 | 36.3 | 27.9 | 31.5 | 33.5 | 26.9 |
| | size | 13×17 | 8×15 | 12×19 | 11×15 | 10×10 | 10×11 | 15×15 | 14×16 | 11×19 |
| | volume | 1436.5 | 480 | 1368 | 907.5 | 500 | 550 | 1687.5 | 1568 | 1149.5 |

TABLE 1-continued

|  |  | Group A | | | Group B | | | group C | | |
| --- | --- | --- | --- | --- | --- | --- | --- | --- | --- | --- |
|  |  | L-00-R-0 | R-00 | — | L-0 | R-000 | L0-R-00 | L-00 | 1-00' | 10-R-00 |
| Day 8 | BW | 28.8 | 33 | 33.4 | 33.2 | 36.6 | 28.7 | 32.7 | 34.1 | 26.6 |
|  | size | 14 × 17 | 10 × 18 | 13 × 22 | 12 × 15 | 10 × 10 | 10 × 12 | 18 × 21 | 16 × 20 | 12 × 19 |
|  | volume | 1666 | 900 | 1859 | 1080 | 500 | 600 | 3402 | 2560 | 1368 |
| Day 9 | BW | 30.2 | 33.3 | 33.8 | 33.5 | 36.6 | 28.8 | 33.3 | 34.2 | 27 |
|  | size | 14 × 20 | 11 × 19 | 14 × 22 | 12 × 15 | 11 × 11 | 11 × 11 | 19 × 20 | 18 × 20 | 12 × 19 |
|  | volume | 1960 | 1149.5 | 2156 | 1080 | 665.5 | 666 | 3610 | 3240 | 1368 |
| Day 10 | BW | 29.5 | 33.6 | 34.1 | 34.1 | 36.7 | 28.7 | 34.5 | 34.4 | 27 |
|  | size | 20 × 21 | 18 × 18 | 17 × 23 | 12 × 15 | 11 × 13 | 11 × 12 | 19 × 21 | 21 × 22 | 12 × 19 |
|  | volume | 4200 | 3078 | 3323.5 | 1080 | 786.5 | 726 | 3790.5 | 4851 | 1368 |
| Day 11 | BW | 30.5 | 34.3 | 35.2 | 34.5 | 36.8 | 29 | 36.6 | 35.1 | 27.7 |
|  | size | 20 × 22 | 20 × 20 | 18 × 25 | 13 × 15 | 11 × 14 | 11 × 12 | 20 × 22 | 21 × 23 | 12 × 20 |
|  | volume | 4400 | 4000 | 4050 | 1267.5 | 847 | 726 | 4400 | 5071.5 | 1440 |
| Day 12 | BW | 31.1 | 35.2 | 35.2 | 35.8 | 37.9 | 29.5 | 37.4 | 35.9 | 28.8 |
|  | size | 22 × 25 | 21 × 23 | 18 × 26 | 13 × 15 | 12 × 14 | 11 × 12 | 21 × 22 | 21 × 24 | 14 × 20 |
|  | volume | 6050 | 4189.5 | 4212 | 1267.5 | 1008 | 726 | 5292 | 4851 | 1960 |

The AZT-QX provided by the invention can selectively kill hepatoma cells, especially hepatoma cells with hepatitis B; the mechanism thereof is relevant to the high expression of thymidine kinase and the suppression of DNA synthesis. Selectivity of the AZT-QX for hepatoma cells is achieved by the Zidovudine part of the molecular structure, while the quinoline part of the structure is the functional group killing the hepatoma cells. Meanwhile, the invention proves that AZT-QX can inhibit the growth of subcutaneous tumor models in mice, and at a low dosage (0.13 mg/kg at a time, twice).

Synthesis of AZT-QX is achieved via a click reaction (see the synthetic scheme above). The comparison compound pip-QX (see structure in FIG. 2) (hereinafter referred to as pip-QX) synthesis is achieved according to the following synthetic route:

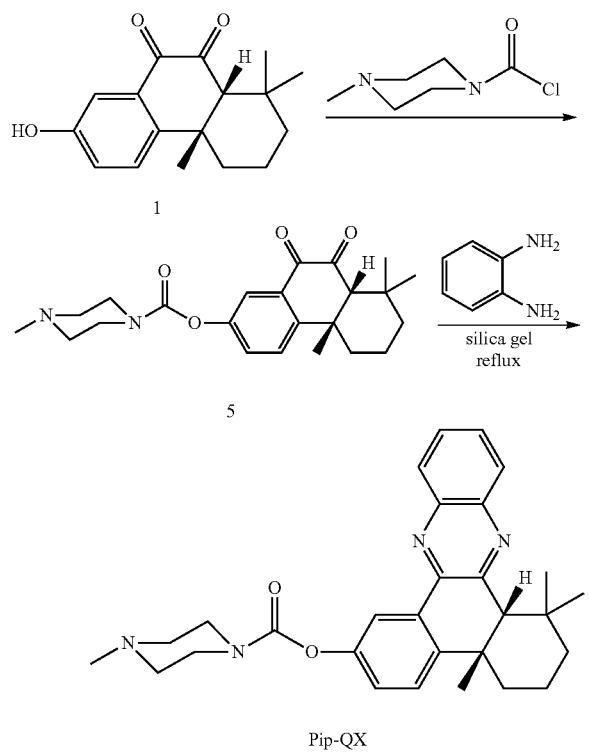

Pip-QX

Selective biological activity of AZT-QX is assessed using cell viability assays MTT on human liver carcinoma cells with hepatitis B Hep3B, hepatoblastoma cell line HepG2 and normal human liver cells HL-7702 (FIG. 3). AZT-QX could effectively kill 80% Hep3B cells at 20 μM (FIG. 3). In contrast, AZT-QX at 200 μM showed no significant toxicity to human normal liver cells HL-7702. The comparison compound Zidovudine illustrates no significant toxicity to all selected cells, while another comparison compound pip-QX killed all the liver cell lines non-selectively (FIG. 3). Under the same conditions, the physical mixture of Zidovudine and pip-QX do not have the characteristic of killing Hep3B cells, which are the hepatoma cells with hepatitis B. In comparison, the toxicity of existing anticancer drug doxorubicin to normal liver cells HL-7702 is more severe than to hepatoma cells (FIG. 3). Therefore, the unique biological activity of AZT-QX selectively killing the hepatoma cells is relevant to its unique chemical structure.

AZT-QX can selectively inhibit nucleic acid synthesis of hepatoma cells with hepatitis B, but does not affect the nucleic acid synthesis of normal liver cells HL-7702. The anti-BrdU fluorescence assay is used to determine the nucleic acid synthesis in cells (FIG. 4). The novel compound AZT-QX effectively inhibits green fluorescence in hepatoma cells, while no such phenomenon in normal liver cells is found (FIG. 4). Our further study illustrates that the comparison compound Zidovudine has no effect in inhibiting nucleic acid synthesis in hepatoma cells; meanwhile, another comparison compound, pip-QX, has an effect similar to AZT-QX. Therefore, the unique biological activity of AZT-QX selectively killing the hepatoma cells is based on the activity of the quinoxaline part, and the selectivity is based on the conjugated Zidovudine structure of AZT-QX.

The mechanism of selective activity of AZT-QX is relevant to the high expression of thymidine kinase. First, it is found that there is no effect on the IC50 concentration of novel compound AZT-QX selectively killing Hep3B hepatoma cells after adding methotrexate, an inhibitor of the thymidine kinase synthesis pathway, and the activity has an additive effect. Secondly, our results of western blots show that the expression of thymidine kinase protein in hepatoma cells is significantly higher than in normal liver cells (FIG. 5). Finally, thymidine kinase in hepatoma cells with hepatitis B is selectively inhibited by siRNA. After AZT-QX is added, the activity thereof is found to be decreased (FIG. 5).

AZT-QX can effectively inhibit the growth of subcutaneous liver tumor models in mice. The liver cancer tumor models are established by subcutaneously injecting H22 hepatoma cells. Once tumors reach an average size of 8.8×8.8 mm, 100 μL saline, Zidovudine (50 μM) or AZT-QX (50 Mm) are injected intratumorally on experimental day 1 and day 7. The figure showing average tumor growth after 12 days (see FIG. 6) illustrates that AZT-QX inhibits tumor growth, while the Zidovudine group is similar to the blank group with saline. The further statistical analysis (see FIG. 6) confirms that as compared with the other two, AZT-QX has greater effectiveness p<0.01, and at a low dosage (0.13 mg/kg at a time, twice).

The experiments above prove that AZT-QX can effectively kill hepatoma cells, especially hepatoma cells with hepatitis B, and can effectively inhibit the growth of subcutaneous tumors; therefore, AZT-QX can be applied in preparing anti-hepatoma drugs.

BRIEF DESCRIPTION OF THE DRAWINGS

FIG. 2 compares the chemical structure of compounds, in which:

FIG. 2(a) is the chemical structure of compared compound Zidovudine (AZT); and

FIG. 2(b) is the chemical structure of compared compound Pip-QX.

FIG. 5 illustrates the mechanism of the novel compound AZT-QX relevant to the high expression of thymidine kinase, in which FIG. 5a illustrates the cell viability after adding methotrexate, an inhibitor of the thymidine kinase synthesis pathway. The inhibitor methotrexate has no effect on the IC50 concentration of novel compound AZT-QX selectively killing Hep3B hepatoma cells, but the activity has an additive effect; FIG. 5b illustrates the experimental results of western blots which illustrate that the expression of the thymidine kinase protein in hepatoma cells is significantly higher than in normal liver cells; FIG. 5c illustrates the selective inhibition of thymidine kinase in hepatoma cells with hepatitis B by siRNA, with western blots then carried out to determine the expression of the thymidine kinase protein in hepatoma cells, confirming siRNA inhibition. FIG. 5d illustrates the cell viability after selective inhibition of thymidine kinase. After selective inhibition of thymidine kinase, AZT-QX is added, resulting in decreased activity. The mechanism of the selective activity of novel compound AZT-QX is relevant to the high expression of thymidine kinase.

FIG. 6 illustrates the average growth of tumors in mice after administration and tumors in mice after 12 days, in which FIG. 6a is a figure of the average growth of tumors in mice; FIG. 6b is contrast of tumors in mice 12 days after different drug treatments. The control is a blank contrast, AZT is Zidovudine, AZT-QX is application of the compound of the invention. The liver cancer tumor models are established by subcutaneously injecting H22 hepatoma cells [see method: Li, et al. Cancer Research 2011, 301,212-220]. Once tumors reach an average size of 8.8×8.8 mm, 100 μL saline, Zidovudine (50 μM) or AZT-QX (50 Mm) are injected intratumorally on experimental day 1 and day 7. During the 12 experimental days, it is show]n that AZT-QX inhibits the tumor growth, while Zidovudine is similar to the blank control; therefore, the novel compound AZT-QX can effectively inhibit the growth of subcutaneous tumor models in mice.

SPECIFIC EMBODIMENTS OF THE INVENTION

Example 1

Figure 1:
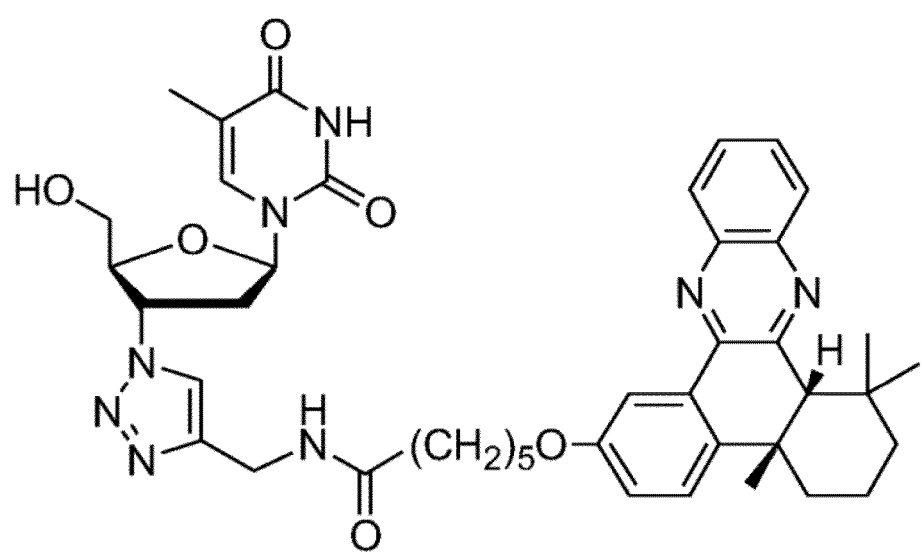
FIG. 1 is the chemical structure of AZT-QX.
Figure 2:
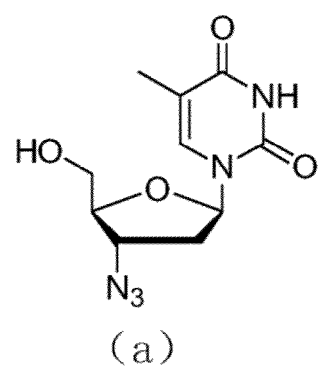
Figure 2:
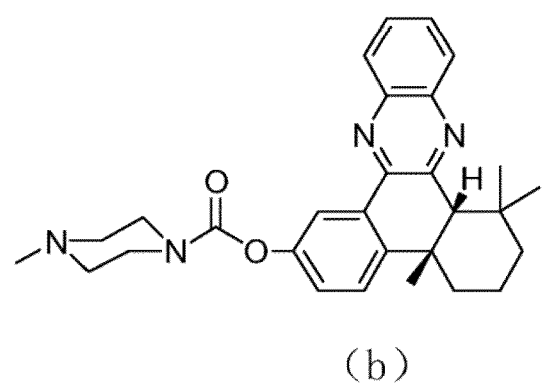
Figure 3:
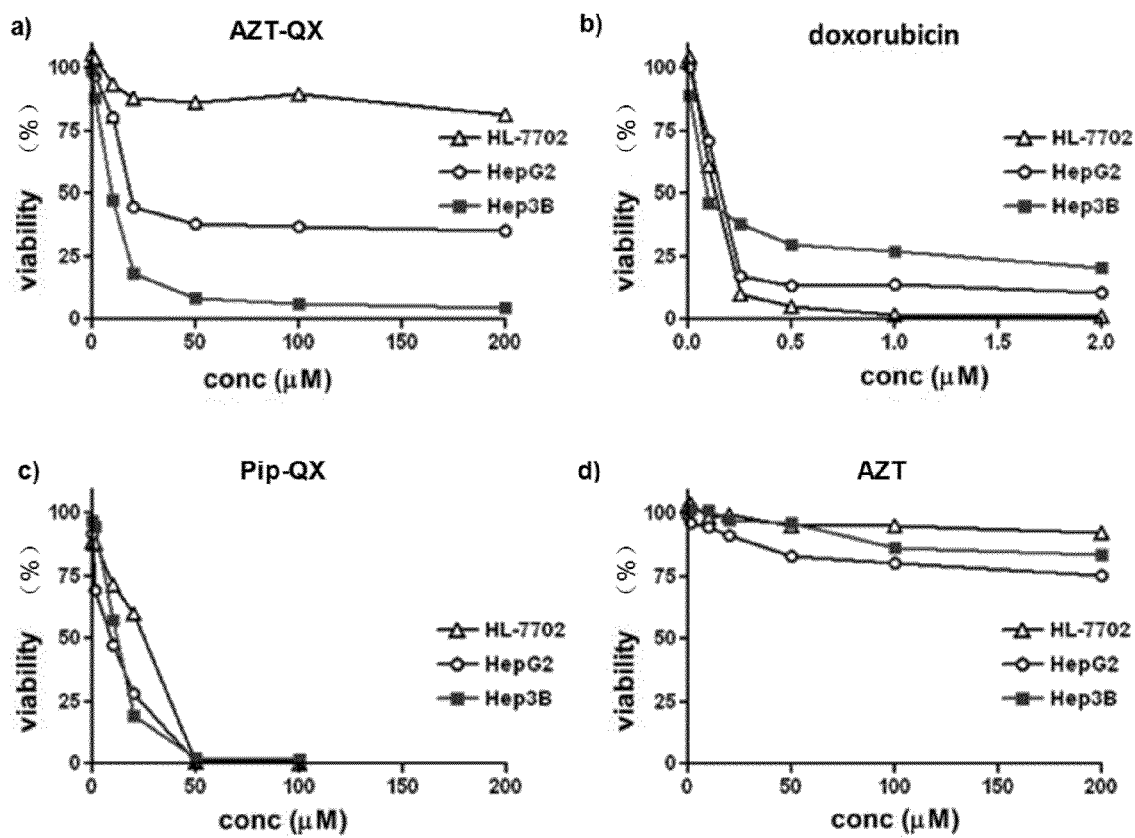
FIG. 3 illustrates determined cell viability of Hep3B hepatoma cells with hepatitis B, a HepG2 hepatoblastoma cell line and HL-7702 normal cancer cells treated with AZT-QX (FIG. 3a), doxorubicin (FIG. 3b), Pip-QX (FIG. 3c), and Zidovudine (FIG. 3d). AZT-QX can effectively kill 80% Hep3B cells at 20 μM. In contrast, AZT-QX illustrates no significant toxicity to normal liver cells HL-7702. The comparison compound Zidovudine illustrates no significant toxicity to all selected cells, while another comparison compound Pip-QX kills all the liver cell line non-selectively. In comparison, the existing anticancer drug doxorubicin has toxicity to normal liver cells HL-7702 being severer than hepatoma cells. AZT-QX has the biological activity of selectively killing the hepatoma cells.
Figure 4:
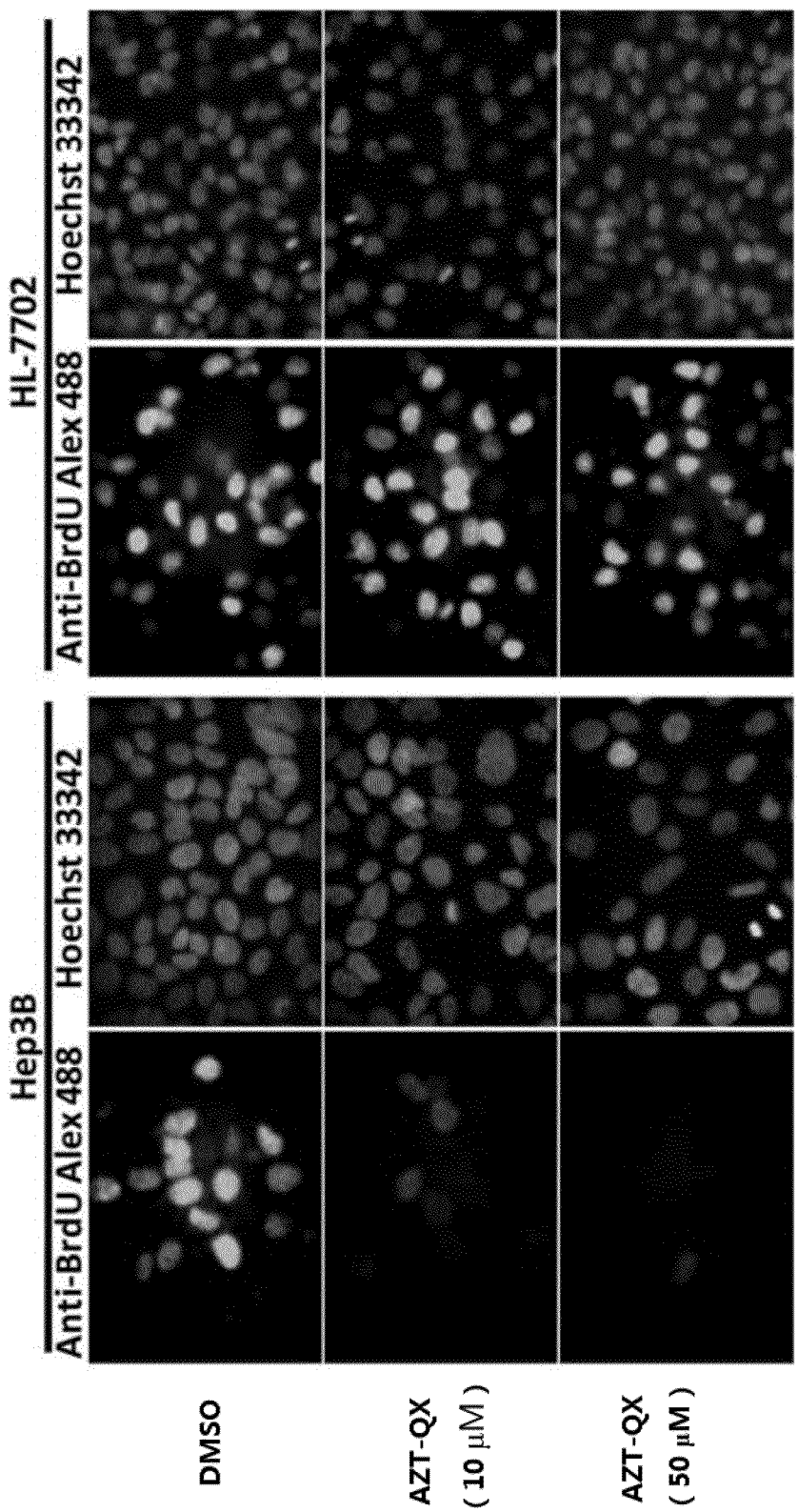
FIG. 4 illustrates fluorescence images of an anti-BrdU assay of nucleic acid synthesis in cells. As shown in the figure, the green fluorescence illustrates the nucleic acid synthesis in cells, and the blue fluorescence illustrates the nuclear staining. The novel compound AZT-QX effectively inhibits green fluorescence in hepatoma cells, while no such phenomenon in normal liver cells is found. AZT-QX can selectively inhibit nucleic acid synthesis in hepatoma cells with hepatitis B, but no effect on nucleic acid synthesis is observed in normal liver cells HL-7702.
Figure 5:
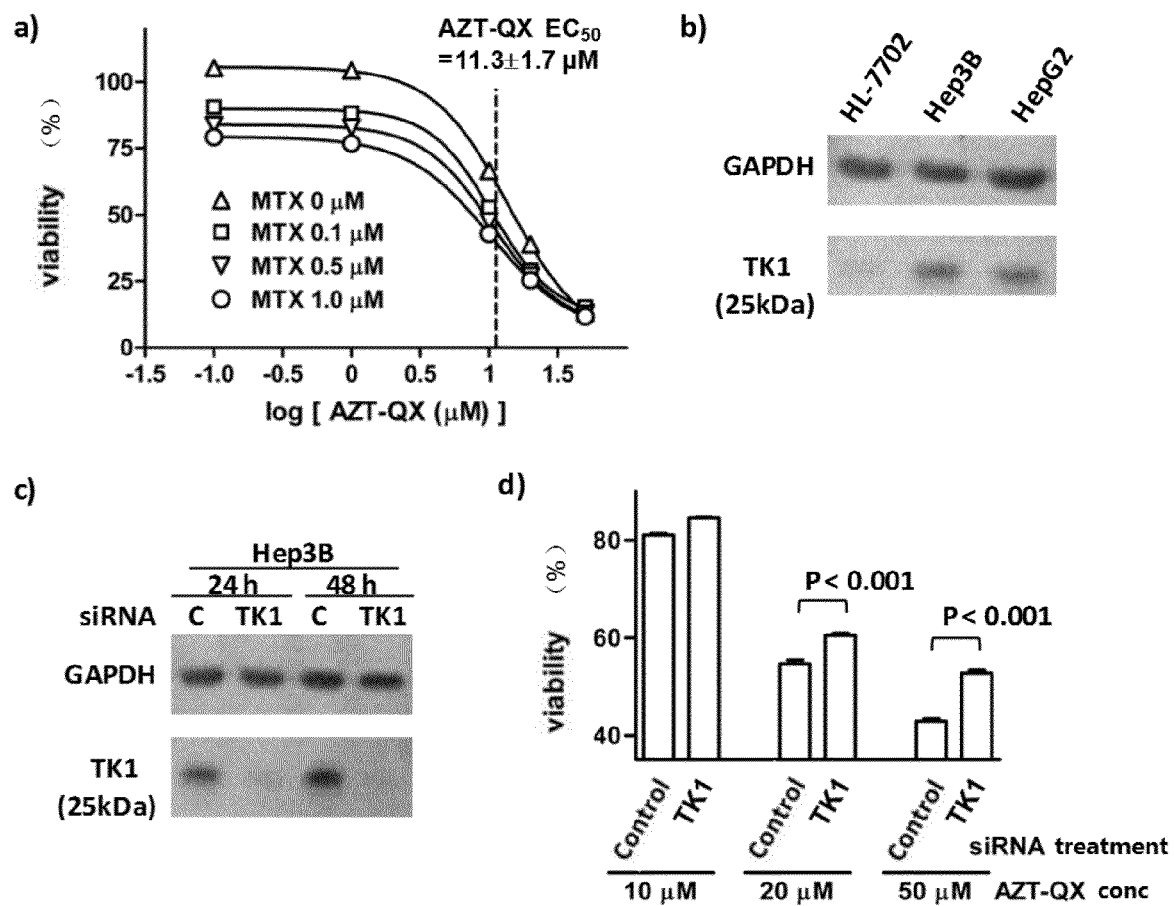
Figure 6:
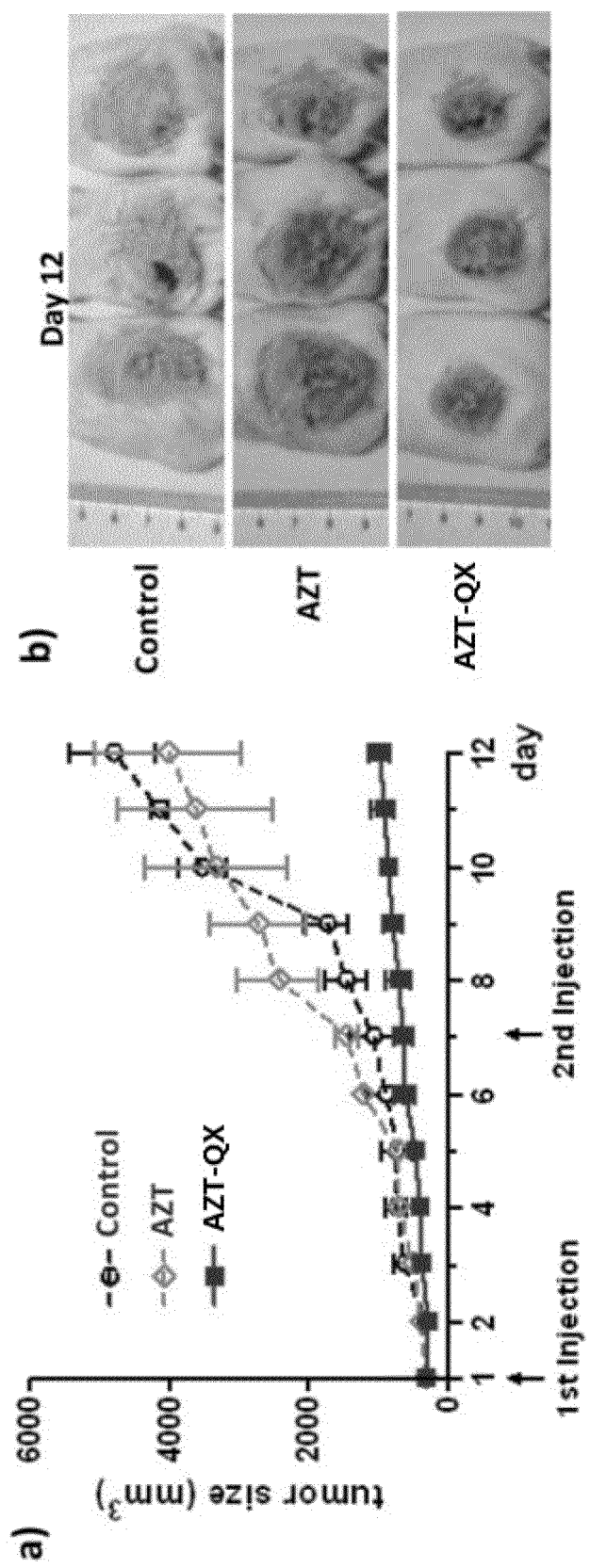
Figure 7:
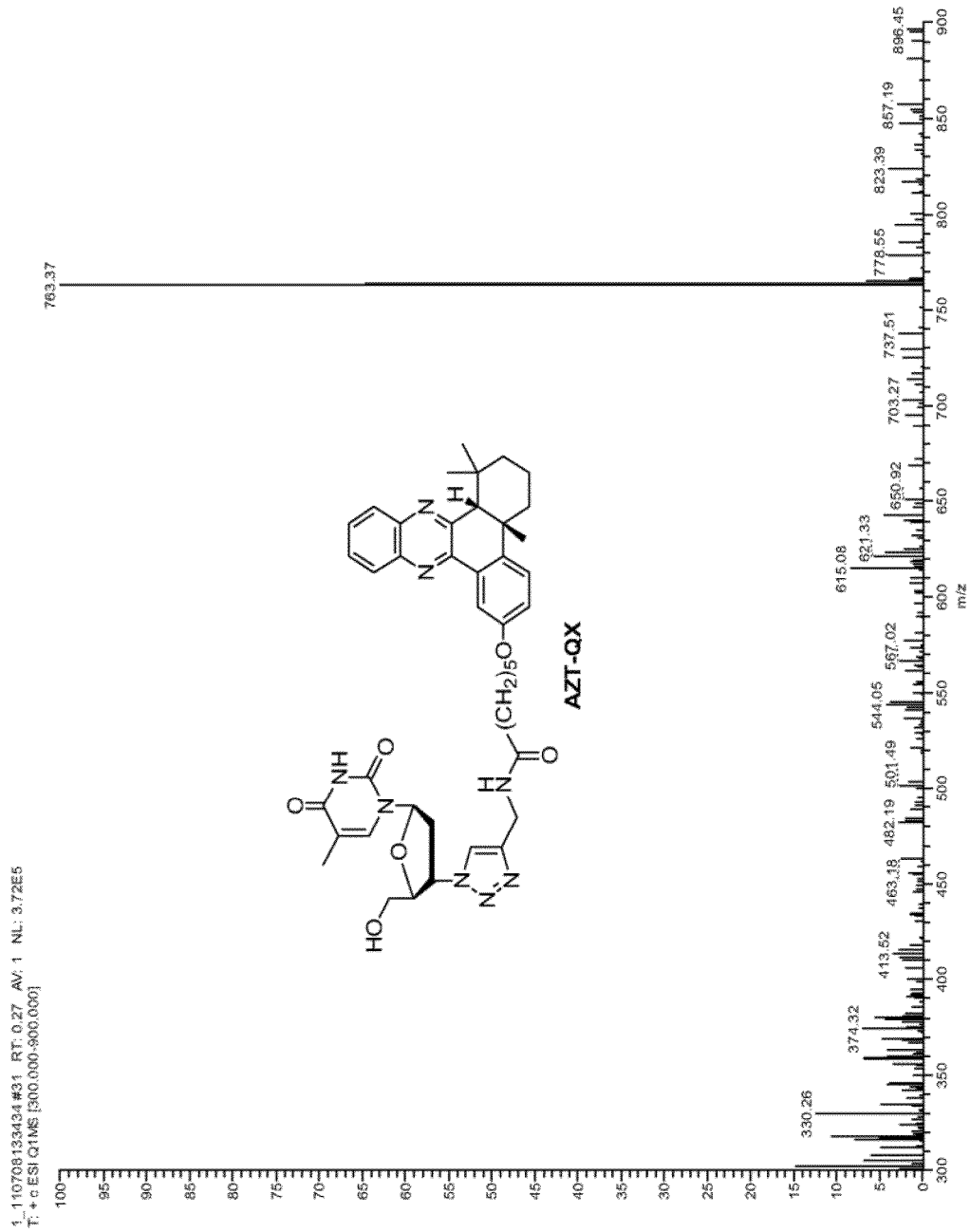
FIG. 7 illustrates mass spectra of AZT-QX.
Figure 8:
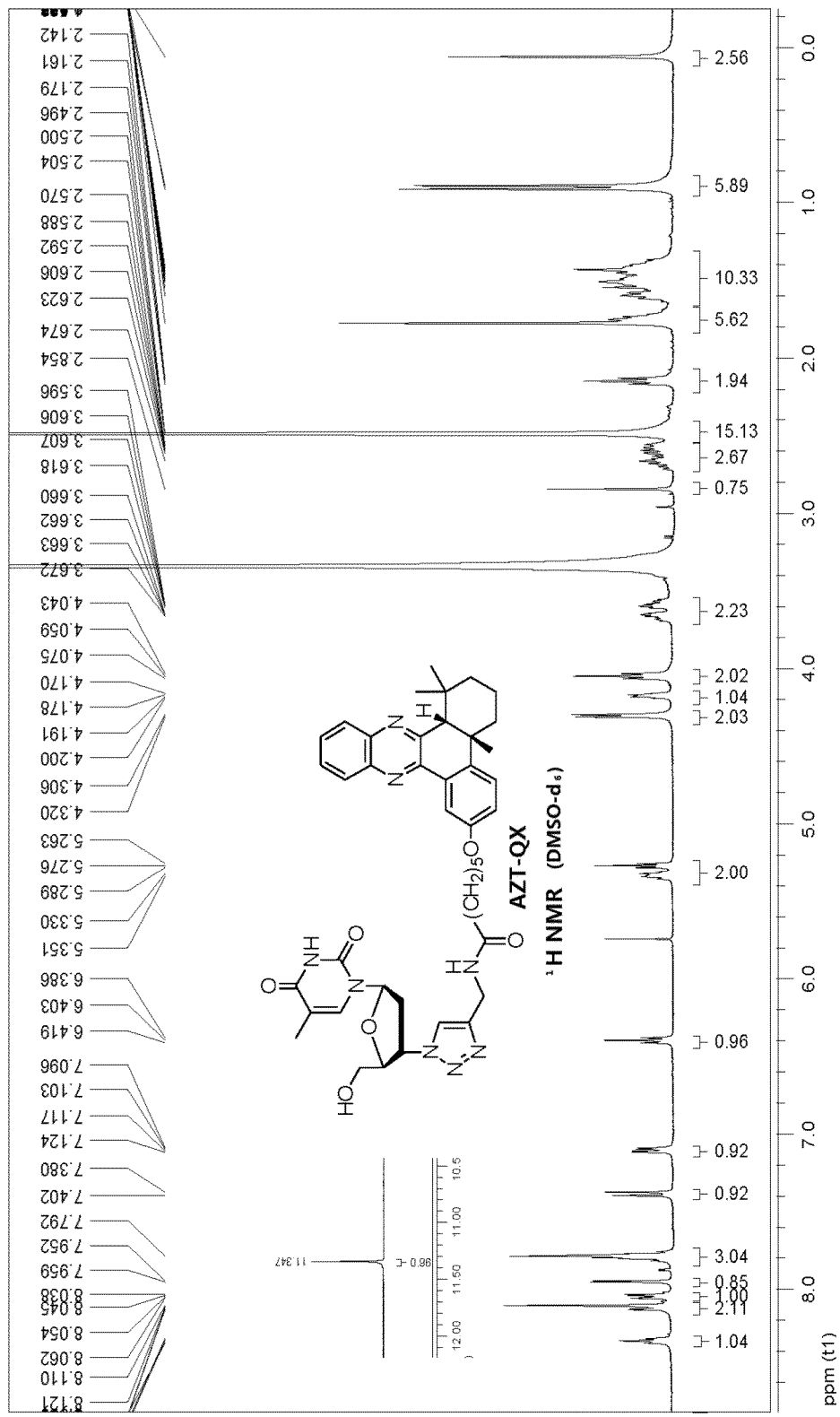
FIG. 8 illustrates hydrogen nuclear magnetic resonance (H-NMR) spectra of AZT-QX.
Figure 9:
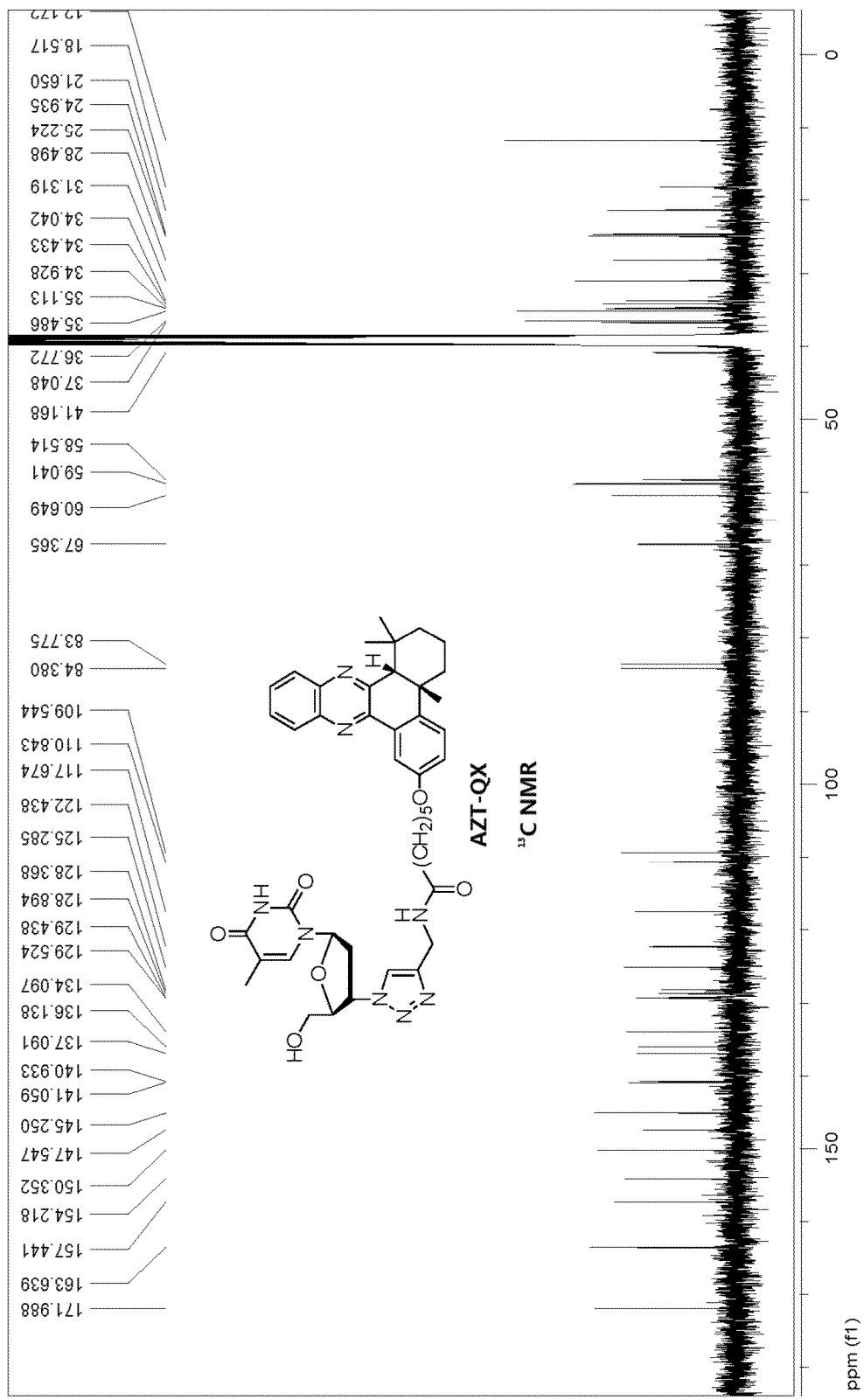
FIG. 9 illustrates carbon nuclear magnetic resonance (C-NMR) spectra of AZT-QX.

Preparation of AZT-QX, Namely the Compound Represented by Formula (I)

Synthesis of AZT-QX, namely the compound represented by formula (I), is achieved via a click reaction; a synthetic route thereof is shown in the following synthesis scheme:

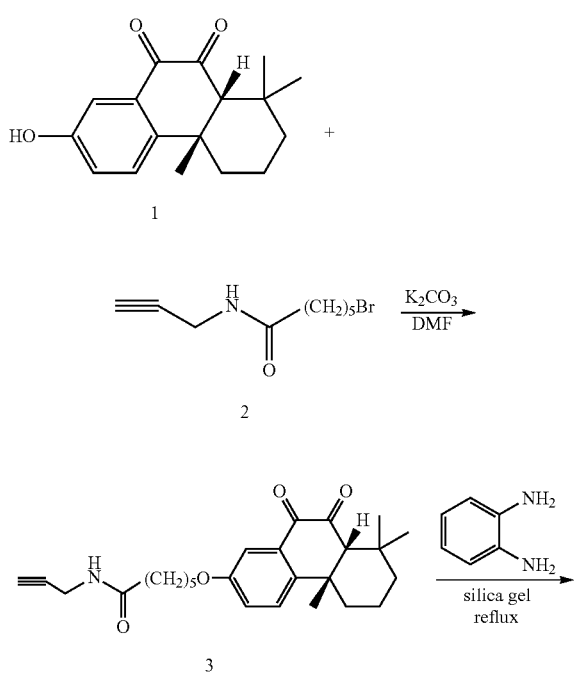

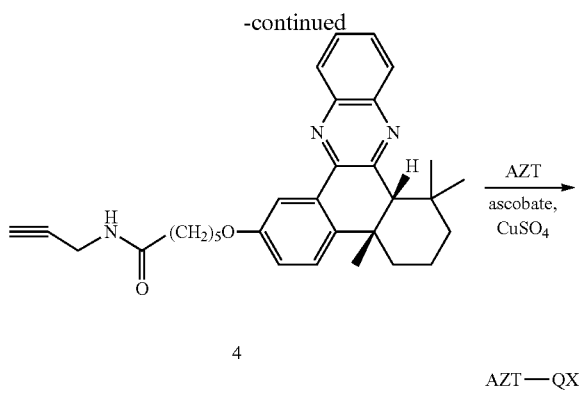

4

AZT → QX

In the synthetic scheme above, compound 1 is 4b,5,6,7,8,8a-cis-hexahydro-2-hydroxy-4-b,8,8a-trimethyl-phenanthrene-9,10-dione; compound 2 is bromo alkyne compound 6-bromo-N-(prop-2-ynyl)hexanamide; compound 3 is N-(prop-2-ynyl)-6-(4 b,8,8-trimethyl-9,10-dioxo-4-b,5,6,7,8,8a,9,10-octahydrophenanthren-2-yloxy)hexanamide; Compound 4 is N-(prop-2-ynyl)-6-(4b,8,8-trimethyl-4-b,5,6,7,8,8a-hexahydrodibenzo[a,c]phenazin-2-yloxy)-hexanamide; product AZ T-QX is N-((1-(2-(hydroxymethyl)-5-(5-methyl-2,4-dioxo-3,4-dihydropyrimidin-1(2H)-yl)-tetrahydrofuran-3-yl)-1H-1,2,3-triazol-4-yl)methyl)-6-(4b,8,8-trimethyl-4-b,5,6,7,8,8a-hexahydrodibenzo[a,c]phenazin-2-yloxy)hexanamide.

A Specific Preparation Method Comprises the Following Steps:

Step 1:

(A) Synthesis of bromo alkyne compound 6-bromo-N-(prop-2-ynyl)hexanamide, namely compound 2 in the synthetic scheme shown above.

To a solution of 6-bromohexanoic acid 694 mg in dichloromethane 50 ml, propargylamine hydrochloride 300 mg, triethylamine 332 mg and 1-(3-dimethylaminopropyl)-3-ethylcarbodiimide are added to perform an acylation reaction, the reaction mixture is stirred under $N_2$ for 16 hours at room temperature, and then the resulting solution is extracted with dichloromethane, and concentrated and purified by $SiO_2$ gel, thereby producing compound 2 390 mg.

(B) Synthesis of N-(prop-2-ynyl)-6-(4b,8,8-trimethyl-9,10-dioxo-4-b,5,6,7,8,8a,9,10-octahydrophenanthren-2-yloxy)hexanamide, namely compound 3 in the synthetic scheme shown above.

Dissolving the compound obtained in Step (A) 390 mg in DMF 20 ml, to the resulting solution, adding 4b,5,6,7,8,8a-cis-hexahydro-2-hydroxy-4-b,8,8a-trimethyl-phenanthrene-9,10-dione 355 mg [See specific synthesis method: Zhou, et al. Chem. Res. Toxicol. 2008,21,732-738] and potassium carbonate to perform a substitution reaction. The reaction mixture is stirred under $N_2$ for 16 hours at room temperature, and then extracted with dichloromethane, and concentrated and purified by $SiO_2$ gel, thereby obtaining Compound 3 320 mg.

Step 2:

Synthesis of N-(prop-2-ynyl)-6-(4b,8,8-trimethyl-4-b,5,6,7,8,8a-hexahydrodibenzo[a,c]-phenazin-2-yloxy)-h exanamide, namely compound 4 in the synthetic scheme shown above.

Dissolving compound 3 obtained in Step 1 320 mg in toluene 20 ml, to the resulting solution, adding o-phenylenediamine 103 mg and $SiO_2$ 300 mg, performing a reaction. The reaction mixture is refluxed under $N_2$ for 18 hours, then concentrated and purified by $SiO_2$ gel, thereby obtaining compound 4 230 mg.

Step 3:

Synthesis of N-((1-(2-(hydroxymethyl)-5-(5-methyl-2,4-dioxo-3,4-dihydropyrimidin-1(2H)-yl)-tetrahydrofuran-3-yl)-1H-1,2,3-triazol-4-yl)methyl)-6-(4b,8,8-trimethyl-4-b,5,6,7,8,8a-hexahydrodibenzo[a,c]phenazin-2-yloxy) hexanamide, namely AZT-QX provided by the invention.

Dissolving compound 4 100 mg in DMF solution 5 ml and dichloromethane 10 ml. To the resulting solution, adding Zidovudine 54 mg and an aqueous solution of sodium ascorbate 40 mM 15 ml. The reaction mixture is purged with $N_2$ for 5 min to remove oxygen, and 10 min, and $CuSO_4 \cdot 5H_2O$ 8 mg is added to perform a click reaction. The reaction mixture is stirred under $N_2$ at room temperature for 16 hours, and then extracted with dichloromethane, and concentrated and purified by $SiO_2$ gel, thereby obtaining AZT-QX 114 mg.

The structural characterization of compounds:

compound 2: $^1H$ NMR (CDCl$_3$, 400 MHz, 1:1 syn/anti): δ=5.71 (br s, 1H; NH), 4.05 (dd, $^3J(H, H)$=5.2 Hz, $^4J(H, H)$=2.5 Hz, 2H; CH$_2$), 3.53 (t, $^3J(H, H)$=6.6 Hz, 1H, 0.5CH$_2$), 3.40 (t, $^3J(H, H)$=6.7 Hz, 1H, 0.5CH$_2$), 2.24-2.19 (m, 3H; CH, CH$_2$), 1.87 (qui, $^3J(H, H)$=7.2 Hz, 1H, 0.5CH$_2$), 1.79 (qui, $^3J(H, H)$=7.0 Hz, 1H, 0.5CH$_2$), 1.67 (qui, $^3J(H, H)$=7.52 Hz, 2H; CH$_2$), 1.50-1.41 ppm (m, 2H; CH$_2$); $^{13}C$ NMR (CDCl$_3$, 100.6 MHz, 1:1 syn/anti): δ=172.3, 172.2, 79.5, 71.6, 44.8, 36.1, 36.1, 33.5, 32.4, 32.2, 29.1, 27.7, 26.4, 24.7, 24.5 ppm; HRMS scaled for $C_9H_{15}BrNO$ [M+H]$^+$232.0337 and [M+2+H]$^+$ 234.0316. found 232.0324 and 234.0413.

compound 3: $^1H$ NMR (CDCl$_3$, 400 MHz): δ=7.53 (d, $^4J(H, H)$=2.9 Hz, 1H; CH), 7.35 (d, $^3J(H, H)$=8.8 Hz, 1H; CH), 7.21 (dd, $^3J(H, H)$=8.7 Hz, $^4J(H, H)$=2.7 Hz, 1H; CH), 5.94 (br s, 1H; NH), 4.04 (dd, $^3J(H, H)$=5.3 Hz, $^4J(H, H)$=2.6 Hz, 2H; CH$_2$), 4.00 (t, $^3J(H, H)$=6.4 Hz, 2H; CH$_2$), 2.65 (s, 1H; CH), 2.53 (d, $^3J(H, H)$=14.3 Hz, 1H, CH), 2.24 (t, $^3J(H, H)$=7.6 Hz, 2H; CH$_2$), 2.21 (d, $^4J(H, H)$=2.5 Hz, 1H; CH), 1.82-1.70 (m, 4H; 2CH$_2$), 1.56-1.31 (m, 7H; 3CH$_2$, CH), 1.18 (s, 3H; CH$_3$), 0.95 (s, 3H; CH$_3$), 0.38 ppm (s, 3H; CH$_3$); $^{13}C$ NMR (CDCl$_3$, 100.6 MHz): δ=199.0, 181.3, 172.4, 158.1, 142.6, 134.6, 126.1, 124.2, 112.6, 71.7, 68.9, 68.1, 41.9, 39.2, 39.0, 36.3, 36.3, 35.5, 31.4, 29.7, 29.2, 28.9, 25.7, 25.2, 24.3, 18.8 ppm; HRMS calcd for $C_{26}H_{34}NO_4$ [M+H]$^+$ 424.2488. found 424.24870 compound 4: $^1H$ NMR (CDCl$_3$, 400 MHz): δ=8.09-8.07 (m, 3H; 3CH), 7.73-7.67 (m, 2H; 2CH), 7.30 (d, $^3J(H, H)$=8.8 Hz, 1H; CH), 7.02 (dd, $^3J(H, H)$=8.4 Hz, $^4J(H, H)$=2.8 Hz, 1H; CH), 5.71 (br s, 1H; NH), 4.14-4.06 (m, 4H; 2CH$_2$), 2.88 (s, 1H; CH), 2.56 (br d, $^3J(H, H)$=14 Hz, 1H, CH), 2.28-2.23 (m, 3H; CH$_2$, CH), 1.89-1.73 (m, 4H; 2CH$_2$), 1.59-1.47 (m, 7H; 3CH$_2$, CH), 1.02 (s, 3H; CH$_3$), 0.99 (s, 3H; CH$_3$), 0.16 ppm (s, 3H; CH$_3$); $^{13}C$ NMR (CDCl$_3$, 100.6 MHz): δ=172.4, 158.0, 154.8, 148.4, 141.9, 141.3, 137.6, 134.8, 129.2, 129.1, 129.0, 128.6, 125.0, 118.1, 111.2, 79.6, 71.6, 67.7, 59.7, 42.0, 37.3, 36.3, 36.1, 36.0, 34.8, 31.5, 29.2, 29.1, 25.8, 25.3, 22.1, 19.0 ppm; HRMS calcd for $C_{32}H_{38}N_3O_2$ [M+H]$^+$ 496.2964. found 496.29640.

AZT-QX: $^1H$ NMR (DMSO-d$_6$, 400 MHz): δ=11.35 (s, 1H; OH), 8.34 (t, $^3J(H, H)$=5.5 Hz, 1H; CH), 8.14-8.11 (m, 2H; 2CH), 8.06-8.04 (m, 1H; CH), 7.96 (d, $^4J(H, H)$=2.8 Hz, 1H; CH), 7.79 (m, 3H; 2CH, NH), 7.39 (d, $^3J(H, H)$=8.7 Hz, 1H; CH), 7.11 (dd, $^3J(H, H)$=8.5 Hz, $^4J(H, H)$=2.8 Hz, 1H; CH), 6.40 (t, $^3J(H, H)$=6.6 Hz, 1H; CH), 5.36-5.33 (m, 1H; CH), 5.28 (t, $^3J(H, H)$=5.2 Hz, 1H; NH), 4.31 (d, $^3J(H, H)$=5.5 Hz, 2H; CH$_2$), 4.18 (m, 1H; CH), 4.06 (t, $^3J(H, H)$=6.4 Hz, 2H; CH$_2$), 3.67-3.60 (m, 2H; CH$_2$), 2.85 (s, 1H; CH), 2.67-2.57 (m, 2H; CH$_2$), 2.16 (t, $^3J(H, H)$=7.4 Hz, 2H; CH$_2$), 1.79-1.62 (m, 5H; CH$_3$, CH$_2$), 1.56-1.43 (m, 10H; 5CH$_2$), 0.93 (s, 3H; CH$_3$), 0.91 (s, 3H; CH$_3$), 0.07 ppm (s, 3H; CH$_3$); $^{13}$C NMR (DMSO-d$_6$, 100.6 MHz): δ=172.0, 163.6, 157.4, 154.2, 150.4, 147.5, 145.2, 141.1, 140.9, 137.1, 136.1, 134.1, 129.5, 129.4, 128.9, 128.4, 125.3, 122.4, 117.7, 110.8, 109.5, 84.4, 83.8, 67.4, 60.6, 59.0, 58.5, 41.2, 37.0, 36.8, 35.5, 35.1, 34.9, 34.4, 34.0, 31.3, 28.5, 25.2, 24.9, 21.6, 18.5, 12.2 ppm; HRMS calcd for C$_{42}$H$_{51}$N$_8$O$_6$ [M+H]$^+$763.3932. found 763.39590.

Example 2

Preparation of Drug Formulation Using AZT-QX as Active Ingredient

An intravenous injection agent using AZT-QX as an active ingredient: AZT-QX is dissolved in DMSO and formulated into a solution at 50 mM. The solution is then diluted 1:1000 in saline and formulated into a solution at 50nM. After filtering and disinfection, the solution can be used as an intravenous injection agent. The recommended dose is 0.13 mg/kg.

What is claimed is:

1. A compound represented by formula (I)

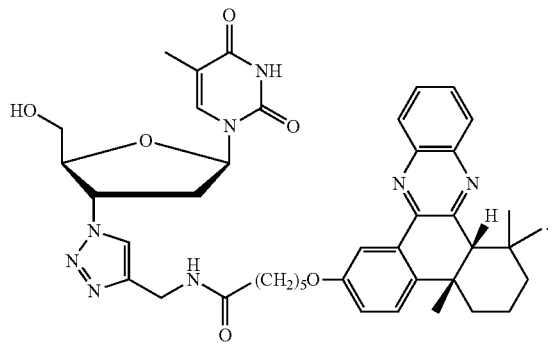

(I)

2. A method for preparing the compound of claim 1, comprising steps of:
Step 1: adding 4b,5,6,7,8,8a-cis-hexahydro-2-hydroxy-4-b,8,8a-trimethyl-phenanthrene-9,10-dione and 6-bromo-N-(prop-2-ynyl)hexanamide into dimethyl formamide (DMF) solution under alkaline condition, thereby producing N-(prop-2-ynyl)-6-(4b,8,8-trimethyl-9,10-dioxo-4-b,5,6,7,8,8a,9,10-octahydrophenanthren-2-yloxy)hexanamide through substitution reaction;
Step 2: condensing a mixture of the produced N-(prop-2-ynyl)-6-(4b,8,8-trimethyl-9,10-dioxo-4-b,5,6,7,8,8a,9,10-octahydrophenanthren-2-yloxy)hexanamide and o-anilines under reflux condition to allow polymerization reaction, thereby obtaining N-(prop-2-ynyl)-6-(4b,8,8-trimethyl-4-b,5,6,7,8,8a-hexahydrodibenzo[a,c]phenazin-2-yloxy)-hexanamide;
Step 3: adding the obtained N-(prop-2-ynyl)-6-(4b,8,8-trimethyl-4-b,5,6,7,8,8a-hexahydrodibenzo[a,c]phenazin-2-yloxy)-hexanamide and Zidovudine in organic solvent to allow click reaction, thereby obtaining the compound of formula (I).

3. The method of claim 2, wherein step 1 is performed by
adding propargylamine hydrochloride, triethylamine and 1-(3-dimethylaminopropyl)-3-ethylcarbodiimide into a solution of 6-bromohexanoic acid and dichloromethane to allow, amidation reaction at room temperature and under N$_2$ for 16 hours, thereby producing a first solution;
extracting the first solution with dichloromethane to produce a second solution
concentrating and purifying the second solution by SiO$_2$ gel, thereby obtaining the 6-bromo-N-(prop-2-ynyl) hexanamide;
dissolving the obtained 6-bromo-N-(prop-2-ynyl)hexanamide in DMF to obtain a third solution;
adding 4b,5,6,7,8,8a-cis-hexahydro-2-hydroxy-4-b,8,8a-trimethyl-phenanthrene-9,10-dione and potassium carbonate to the third solution to allow substitution reaction under N$_2$ for 16 hours at room temperature, thereby obtaining a fourth solution;
extracting the fourth solution with dichloromethane to obtain a fifth solution;
concentrating and purifying the fifth solution by SiO$_2$ gel, thereby obtaining N-(prop-2-ynyl)-6-(4b,8,8-trimethyl-9,10-dioxo-4-b,5,6,7,8,8a,9,10-octahydrophenanthren-2-yloxy)hexanamide.

4. The method of claim 2, wherein step 2 is performed by
dissolving N-(prop-2-ynyl)-6-(4b,8,8-trimethyl-9,10-dioxo-4-b,5,6,7,8,8a,9,10-octahydrophen-anthren-2-yloxy)hexanamide obtained in step 1 in toluene to obtain a sixth solution;
adding o-phenylenediamine and SiO$_2$ to the sixth solution which is refluxed under N$_2$ for 18 hours to obtain a seventh solution;
concentrating and purifying the seventh solution by SiO$_2$ gel, and thus obtaining N-(prop-2-ynyl)-6-(4b,8,8-trimethyl-4-b,5,6,7,8,8a-hexahydrodibenzo[a,c]phenazin-2-yloxy)-hexanamide.

5. The method of claim 2, wherein step 3 is performed by
dissolving N-(prop-2-ynyl)-6-(4b,8,8-trimethyl-4-b,5,6,7,8,8a-hexahydrodibenzo[a,c]phenazin-2-yloxy)-hexanamide obtained in step 2 in 5 ml DMF and dichloromethane solution to obtain a eighth solution;
adding Zidovudine and an aqueous solution of sodium ascorbate to the eighth solution to obtain a reaction mixture;
purging the reaction mixture with N$_2$ for 5 min to remove oxygen;
adding CuSO$_4$ to the reaction mixture to allow click reaction at room temperature under N$_2$ for 16 hours;
extracting the reaction mixture with dichloromethane;
concentrating and purifying the reaction mixture by SiO$_2$ gel, and thus obtaining the compound of formula (I).

6. The compound of claim 1 used to prepare an anti-hepatoma drug formulation.

7. An anti-hepatoma drug comprising the compound of claim 1 as an active ingredient.

8. An anti-hepatoma drug formulation comprising the compound of claim 1 and pharmaceutically acceptable carriers, excipients or additives.

9. An anti-hepatoma drug formulation comprising the compound of claim 1 as an active ingredient, wherein the anti-hepatoma drug formulation is an intravenous injection agent.

* * * * *